United States Patent [19]

Hagen et al.

[11] 4,283,561
[45] Aug. 11, 1981

[54] MIXTURE OF ALDEHYDES RESULTING FROM HYDROFORMYLATION OF α-TERPINENE

[75] Inventors: Jens Hagen, Ketsch; Klaus Bruns, Krefeld-Traar, both of Fed. Rep. of Germany

[73] Assignee: Henkel Kommanditgesellschaft auf Aktien, Düsseldorf-Holthausen, Fed. Rep. of Germany

[21] Appl. No.: 94,277

[22] Filed: Nov. 14, 1979

[30] Foreign Application Priority Data

Nov. 16, 1978 [DE] Fed. Rep. of Germany ....... 2849642

[51] Int. Cl.³ .............................................. C07C 47/42
[52] U.S. Cl. .................................. 568/446; 568/444; 252/522 R
[58] Field of Search ................. 260/598; 568/444, 446

[56] References Cited

U.S. PATENT DOCUMENTS

| | | | |
|---|---|---|---|
| 2,880,241 | 3/1959 | Hughes | 260/598 X |
| 3,239,566 | 3/1966 | Slaugh et al. | 260/598 X |
| 3,499,932 | 3/1970 | Pruett et al. | 260/598 |

FOREIGN PATENT DOCUMENTS 151446  5/1953  Australia ................................ 568/444

OTHER PUBLICATIONS

Clement et al., I. & E. C. (Product Research and Development), vol. 4, (1965), 283–286.

*Primary Examiner*—Bernard Helfin
*Attorney, Agent, or Firm*—Hammond & Littell, Weissenberger and Muserlian

[57] ABSTRACT

This invention is directed to a mixture of compounds of formulas

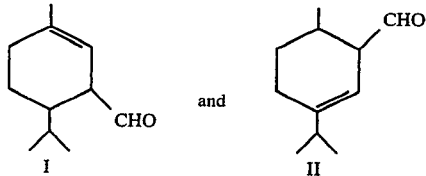

This invention is also directed to preparation of the mixture and the use of said mixture as a perfuming agent.

1 Claim, No Drawings

MIXTURE OF ALDEHYDES RESULTING FROM HYDROFORMYLATION OF α-TERPINENE

FIELD OF THE INVENTION

This invention is directed to novel aldehydes. More particularly, this invention is directed to aldehydes prepared by the hydroformylation of α-terpinene and the use of such aldehydes as perfuming agents.

OBJECTS OF THE INVENTION

It is an object of this invention to provide a mixture of novel aldehydes.

It is also an object of this invention to provide for the preparation of such aldehydes by the hydroformylation of α-terepinene.

It is further an object of the invention to provide for the use of such aldehydes as perfuming agents.

These and other objects of the invention will become more apparent in the discussion below.

DESCRIPTION OF THE INVENTION

It has surprisingly been found that novel aldehydes can be prepared by the hydroformylation of α-terpinene. These aldehydes comprise a mixture of compounds of formulas

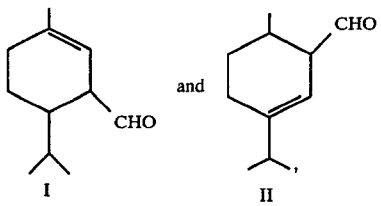

and these compounds constitute valuable new perfumes with salicylate and cumin-perilla note and of extraordinary retentivity.

The production of the mixture of the compounds of Formulas I and II is effected expediently by reaction of α-terpinene with carbon monoxide and hydrogen at from about 70° to 160° C. and under a pressure of from about 100 to 400 bar. Mixtures of tertiary phosphines and rhodium carbonyl complexes containing these tertiary phosphines are useful as catalysts.

Suitable tertiary phosphines include trialkyl phosphines whose alkyl radicals have from 1 to 20 carbon atoms, as well as triphenyl phosphines wherein the phenyl radicals may be substituted by alkyl or alkoxy groups with from 1 to 4 carbon atoms, triphenyl phosphine being preferred. In the catalyst mixtures, the molar number of total phosphine present per gram atom of rhodium is in the range of from about 20 to 200.

The exact composition of the catalytically active rhodium carbonyl complexes is not known. Presumably, however, they involve rhodium complexes in which one or more carbonyl ligands have been replaced by phosphine ligands.

The actually active rhodium carbonyl complex compound is formed in each case in situ under the conditions of hydroformylation. The quantity of rhodium required for this purpose can be supplied to the reaction mixture in the form of suitable rhodium compounds, such as rhodium chloride, rhodium oxide, rhodium salts of fatty acids, rhodium chelates, rhodium carbonyl, or dimeric rhodium carbonyl chloride, or mixtures thereof. Preferably rhodium complexes are used in which the phosphine is already present in the catalyst mixture as ligands, such as, for example, the compound $RhCl(CO)[P(C_6H_5)_3]_2$.

The rhodium compounds are advantageously used in such quantities of from about 5 to 5000, preferably from about 15 to 400, ppm, calculated as metal, based on the α-terpinene present.

Although the reaction can be carried out in the absence of solvents, it has proven expedient to use solvents. Useful solvents include saturated hydrocarbons of from about 1 to 8 carbon atoms, such as pentane, hexane, heptane, and cyclohexane; aromatics such as benzene, toluene, and xylene; cyclic ethers such as tetrahydrofuran and dioxane; alcohols such as methanol, ethanol, and isopropanol; and diols such as ethylene glycol and propylene glycol. Preferably the hydroformylation is carried out in saturated hydrocarbons or cyclic ethers.

The compounds of Formulas I and II are recovered from the reaction mixture by distillation, which is advantageously carried out in an inert gas atmosphere, such as, for example, a nitrogen atmosphere.

The reaction product formed in the described hydroformylation of α-terpinene constitutes a mixture of the aldehydes of Formulas I and II. The mixture has perfuming properties and can be mixed with other perfumes in various quantity ratios to prepare new perfume compositions. Generally, the proportion of the mixture in the perfume compositions will range from about 1 to 50 percent by weight, based on the weight of the total composition. Such compositions can serve directly as perfume or they can be used as perfuming agents in cosmetics, such as creams, lotions, toilet waters, aerosols, toilet soaps, and the like. Also, the mixture may be used to improve the odor of technical products such as detergents and cleansing agents, softeners, textile treatment agents, and the like. To perfume the various products, the perfume compositions containing the mixtures according to the invention are added to such products in concentrations of from about 0.05 to 2 percent by weight, based on the weight of the total product.

The following example is intended to illustrate the invention and is not to be construed as limiting the invention thereto.

EXAMPLE

In a five liter stroke agitator autoclave of stainless steel, 272 g (2 mols) of α-terpinene, 3.8 g (14.5 mmole) of $P(C_6H_5)_3$, 0.2 g (0.29 mmole) of $RhCl(CO)[P(C_6H_5)_3]_2$, and 750 ml of tetrahydrofuran were mixed together.

The autoclave was flushed with synthesis gas. Thereafter, a gaseous mixture consisting of equal volumes of hydrogen and carbon monoxide was introduced to result in a pressure of 200 bar. The autoclave contents were heated to 130° C. under stirring, maintained at from 130° to 140° C. for 5 hours, and then cooled to room temperature. Tetrahydrofuran was distilled from the reaction mixture under waterjet vacuum. In the distillation of the residue under oil pump vacuum, 225 g of product distilled at 98° to 100° C. at 20 mbar (68% of the theory).

A gas chromatography analysis showed that the product constituted a two-component mixture.

Carbonyl number: 170 (theory, 168.7).

The product showed the following IR Spectrum (film): 3005 cm$^{-1}$; 1682 cm$^{-1}$

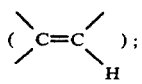

2700 cm$^{-1}$; 1725 cm$^{-1}$ (CHO); 1380 cm$^{-1}$; 1360 cm$^{-1}$; 845 cm$^{-1}$ (C=C tri-substituted).

Odor: Salicylate note, cumin-perilla note.

The preceding specific embodiments are illustrative of the practice of the invention. It is to be understood, however, that other expedients known to those skilled in the art, or disclosed herein, may be employed without departing from the spirit of the invention or the scope of the appended claims.

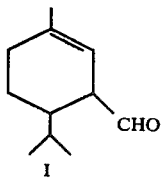 and 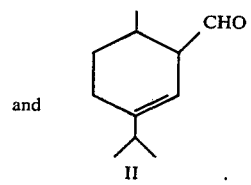

We claim:

1. A mixture consisting of the compounds of formulas